US012651662B2

(12) United States Patent
Yu et al.

(10) Patent No.: US 12,651,662 B2
(45) Date of Patent: Jun. 9, 2026

(54) DISSIMILAR-PAIRED NEURAL NETWORK ARCHITECTURE FOR DATA SEGMENTATION

(71) Applicant: The University of Hong Kong, Hong Kong (CN)

(72) Inventors: Philip Leung Ho Yu, Hong Kong (CN); Jia You, Hong Kong (CN); Anderson Chun On Tsang, Hong Kong (CN); Gilberto Ka Kit Leung, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 422 days.

(21) Appl. No.: 18/252,480

(22) PCT Filed: Nov. 24, 2021

(86) PCT No.: PCT/CN2021/132919
§ 371 (c)(1),
(2) Date: May 10, 2023

(87) PCT Pub. No.: WO2022/111546
PCT Pub. Date: Jun. 2, 2022

(65) Prior Publication Data
US 2024/0006056 A1 Jan. 4, 2024

Related U.S. Application Data

(60) Provisional application No. 63/118,275, filed on Nov. 25, 2020.

(51) Int. Cl.
*G06K 9/00* (2022.01)
*G06N 3/0455* (2023.01)
(Continued)

(52) U.S. Cl.
CPC ........... *G16H 30/40* (2018.01); *G06N 3/0455* (2023.01); *G16H 30/20* (2018.01)

(58) Field of Classification Search
CPC ...... G16H 30/40; G16H 30/20; G06N 3/0455; G06N 3/045; G06N 3/0464; G06N 3/09; G06N 3/048; G06N 3/08
See application file for complete search history.

(56) References Cited

U.S. PATENT DOCUMENTS

2012/0114205 A1 5/2012 Tang
2019/0147320 A1* 5/2019 Mattyus ............... G06V 20/182
382/155
2021/0312674 A1* 10/2021 Abrol ..................... G06N 3/045

FOREIGN PATENT DOCUMENTS

CN 111724397 9/2020
WO WO-2020232124 A1 * 11/2020 ........... A61B 5/7267

OTHER PUBLICATIONS

Agrawal, "Dissimilarity learning via Siamese network predicts brain imaging data", Centre for BioSSystems Science & Engineering, (2019).

(Continued)

*Primary Examiner* — Xin Jia
(74) *Attorney, Agent, or Firm* — PABST PATENT GROUP LLP

(57) ABSTRACT

A computer-implemented system (CIS) is provided for processing and/or analyzing non-contrast-enhance computer tomography medical imaging input data is described. The CIS contains (i) twin U-Net architectures with equal weights, which are built on a Siamese architecture, and (ii) a Dissimilar block operably linked to the two U-Net architectures, and built on top of the Siamese-U-Net architecture to form a Dissimilar-Siamese-U-Net architecture. The computer-implemented system can be used in diagnosing acute ischemic stroke and/or thromboembolus, by analyzing (Continued)

separate and independent input images of the left and right hemispheres of a brain. The diagnosis is based on a detection of the presence of a hyperdense middle cerebral artery sign.

20 Claims, 5 Drawing Sheets

(51) Int. Cl.
  *G16H 30/20*        (2018.01)
  *G16H 30/40*        (2018.01)

(56)                References Cited

OTHER PUBLICATIONS

Badrinarayanan, et al., "SegNet: A Deep Convolutional Encoder-Decoder Architecture for Image Segmentation", IEEE trans. Pattern Anal. Mach. Intell., 39 (12): 2481-2495 (2017).

Barber, et al., "Hyperdense Sylvian Fissure MCA 'Do' Sign", Stroke, 32 (1): 84-88 (2001).

Barber, et al., "Validity and reliability of a quantitative computed tomography score in predicting outcome of hyperacute stroke before thrombolytic therapy", The Lancet, 355 (9216): 1670-1674 (2000).

Chen, et al., "Encoder-Decoder with Atrous Separable Convolution for Semantic Image Segmentation", Proc. Eur. Conf Comput. Vis., 801-818 (2018).

Christ, et al., "Automatic Liver and Lesion Segmentation in CT Using Cascaded Fully Convolutional Neural Networks and 3D Conditional Random Fields", Medical Image Computing and Computer-Assisted Intervention—MICCAI 2016: 19th International Conference, 415-423 (2016).

Coudray, et al., "Classification and mutation prediction from non-small cell lung cancer histopathology images using deep learning", Nature Med, 24(10): 1559-1567 (2018).

Dong, et al., "MobileXNet: An Efficient Convolutional Neural Network for Monocular Depth Estimation", Proc. IEEE Conj Comput. Vis. Pattern Recognit., 1851-1860 (2017).

Ernst, et al., "Sensitivity of visual and quantitative detection of middle cerebral artery occlusion on non-contrast-enhanced computed tomography", Neuroradiology, 56(12): 1063-1068 (2014).

Han, et al., "Keratinocytic Skin Cancer Detection on the Face Using Region-Based Convolutional Neural Network", JAMA Dermatology, 156 (1): 29 (2019).

Havael, et al., "Brain tumor segmentation with Deep Neural Networks", Med Imag. Anal., 35: 18-31 (2017).

He, et al., "Delving deep into rectifiers: Surpassing human-level performance on ImageNet classification", Proc. IEEE Int. Conf. Comput. Vis. (ICCV), 1026-1034 (2015).

Jauch, et al., "Guidelines for the Early Management of Patients With Acute Ischemic Stroke", Stroke, 44(3): 870-947 (2013).

Jenkinson, et al., "FSL", Neuroimage, 62(2): 782-790 (2012) Uncorrected Proof.

Koch, et al., "Siamese Neural Networks for One-shot Image Recognition", Proceedings of the 32 nd International Conference on Machine Learning, Lille, France, 2015. JMLR: W&CP, 37 (2015).

Kooi and Karssemeijer, "Classifying symmetrical differences and temporal change for the detection of malignant masses in mammography using deep neural networks", J Med Imaging, 4(4): 044501 (2017).

Kuang, et al., "Automated infarct segmentation from follow-up noncontrast CT scans in patients with acute ischemic stroke using dense Multi-Path Contextual Generative Adversarial Network", In: Shen D, et al., editors. Proc. Medical Image Computing and Computer Assisted Intervention MICCAI 2019. Lecture Notes in Computer Science, 11766: 856-863 (2019).

Lisowska, et al., "Context-aware convolutional neural networks for stroke sign detection in non-contrast CT scans", In M. Valdés Hernández, & V. González-Castro (Eds.), Medical Image Understanding and Analysis: MIUA 2017, Communications in Computer and Information Science, 723: 494-505 (2017).

Litjens, et al., "A survey on deep learning in medical image analysis", Med Image Anal., 42: 60-88 (2017).

Löber, et al., "Automatic thrombus detection in non-enhanced computed tomography images in patients with acute ischemic stroke", Proc. Vis. Comput. Biol. Med Workshop, 125-129 (2017).

Long, et al., "Fully Convolutional Networks for Semantic Segmentation", IEEE Conference on Computer Vision and Pattern Recognition (CVPR), 3431-3440 (2015).

Maldjian, et al., "Automated CT Segmentation and Analysis for Acute Middle Cerebral Artery Stroke", Amer. J of Neuroradiology, 22(6): 1050-1055 (2001).

Marks, et al., "Evaluation of Early Computed Tomographic Findings in Acute Ischemic Stroke", Stroke, 30(2): 389-392 (1999).

Muschelli, et al., "Reduction of motion-related artifacts in resting state fMRI using aCompCor". Neuroimage, 114: 375-385 (2015).

Powers, et al., "Guidelines for the Early Management of Patients With Acute Ischemic Stroke: 2019 Update to the 2018 Guidelines for the Early Management of Acute Ischemic Stroke: A Guideline for Healthcare Professionals From the American Heart Association/American Stroke Association", Stroke, 50(12): e344-e418 (2019).

Qiu, et al., "Machine Learning for Detecting Early Infarction in Acute Stroke with Non-Contrast-enhanced CT", Radiology, 294(3): 638-644 (2020).

Riedel, et al., "Assessment of Thrombus in Acute Middle Cerebral Artery Occlusion Using Thin-Slice Nonenhanced Computed Tomography Reconstructions", Stroke, 41(8): 1659-1664 (2010).

Ronneberger, et al., "U-net: Convolutional Networks for Biomedical Image Segmentation", In: International Conference on Medical Image Computing and Computer-Assisted Intervention, 234-241.

Saddique, et al., "A Hybrid Approach of Using Symmetry Technique for Brain Tumor Segmentation", Comput. and Math. Methods in Med, 2014(712783): 1-10 (2014).

Salehi, et al., "Tversky Loss Function for Image Segmentation Using 3D Fully Convolutional Deep Networks", In: Wang, et al., (eds) Machine Learning in Medical Imaging. MLMI 2017. Lecture Notes in Computer Science, 10541: 379-387 (2017).

Smith, et al., "Advances in functional and structural MR image analysis and implementation as FSL", Neuroimage, 23(Suppl. 1): 208-219 (2004).

Tsang, et al., "Burden of large vessel occlusion stroke and the service gap of thrombectomy: A population-based study using a territory-wide public hospital system registry", Int. J of Stroke, 15(1): 69-74 (2019).

Von Kummer, et. al., "Sensitivity and prognostic value of early CT in occlusion of the middle cerebral artery trunk", Amer. J of Neuroradiology, 15(1): 9-15 (1994).

You, et al., "Automated Hierarchy Evaluation System of Large Vessel Occlusion in Acute Ischemia Stroke", Frontiers in Neuroinformatics, 14: 13 (2020).

Zhao, et al., "Pyramid Scene Parsing Network", Proc. IEEE Conj Comput. Vis. Pattern Recognit., 2881-2890 (2017).

Zhou, et al., "UNet++: A Nested U-Net Architecture for Medical Image Segmentation", Deep Learn Med Image Anal Multimodal Learn Clin Decis Support, 11045: 3-11 (2018).

International search report for corresponding PCT/CN2021/132919 dated Feb. 1, 2022.

Abul-Kasim, et al., "Hyperdense middle cerebral artery sign in multidetector computed tomography: definition, occurrence, and reliability analysis", Neurology India, 57(2): 143 (2009).

Kim, et al., "Clinical implications of CT hyperdense artery sign in patients with acute middle cerebral artery occlusion in the era of modern mechanical thrombectomy", J of Neurology, 264(12): 2450-2456 (2017).

Lim, et al., "The CT-Defined Hyperdense Arterial Sign as a Marker for Acute Intracerebral Large Vessel Occlusion", J of Neuroimaging, 28(2): 212-216 (2017).

Lucas, et al., "Automatic Detection and Segmentation of the Acute Vessel Thrombus in Cerebral CT", Proc. Informatik aktuell Bildverarbeitung fur die Medizin 2019, 74-79 (2019).

(56)     References Cited

OTHER PUBLICATIONS

Man, et al., "The Location of Pretreatment Hyperdense Middle Cerebral Artery Sign Predicts the Outcome of Intraarterial Thrombectomy for Acute Stroke", J of Neuroimaging, 25(2): 263-268 (2014).

Takahashi, et al., "An automated detection method for the MCA dot sign of acute stroke in unenhanced CT", Radial. Phys. Technol, 7(1): 79-88 (2014).

* cited by examiner

Convolution (3 X 3 X 3)
+ PReLU

Max Pooling (2 X 2 X 2)

Upsampling (2 X 2 X 2)

Concatenation

····⊕·➤   Skip Connections $F_k^*$   Encoded Feature Maps
\* : left or right sub-network
$k$ : $k$-th encoding block
e.g. 1, 2, 3, 4 or 5

$f(F_k^L, F_k^R)$   $k$-th Dissimilar Block $$= |F_k^L - F_k^R|$$

Iterations

Iterations

DISSIMILAR-PAIRED NEURAL NETWORK ARCHITECTURE FOR DATA SEGMENTATION

CROSS-REFERENCE TO RELATED APPLICATIONS

This application is a National Phase application under 35 U.S.C. § 371 of PCT/CN2021/132919, filed Nov. 24, 2021, and claims the benefit of and priority to U.S. Application No. 63/118,275 filed Nov. 25, 2020, the disclosures of which are hereby incorporated herein by reference in their entirety.

FIELD OF THE INVENTION

This invention is generally related to processing and visualizing data, particularly a computer-implemented system/method for processing and visualizing images of the left and right hemispheres of the brain in clinical settings, to determine the presence of a hyperdense middle cerebral artery sign that is indicative of acute ischemic stroke.

BACKGROUND OF THE INVENTION

Acute ischemic stroke (AIS) is a leading cause of death and substantial disability over the world (Powers, et al., *Stroke* 2019, 50 (12), e344-e418). Non-contrast-enhanced computer tomography (NCCT) is recommended by the American Heart Association as the first-line diagnostic test for emergency evaluation of AIS detection due to its widespread availability, speed of imaging, low cost and patient tolerance (Jauch, et al., *Stroke* 2013, 44 (3), 870-947). The hyperdense middle cerebral artery sign (HMCAS) indicative of a thromboembolus has been declared as a vital computer tomography finding for intravascular thrombus in the diagnosis of AIS (Marks, et al., *Stroke* 1999, 30 (2), 389-392; Lim, et al., *J. of Neuroimaging* 2017, 28 (2), 212-216; Barber, et al., *Stroke* 2001, 32 (1), 84-88). The hyperdensity has been associated with embolic occlusion of branches of the middle cerebral artery in the sylvian fissure (Barber, et al., *Stroke* 2001, 32 (1), 84-88). Accurate quantification of the extent of ischemic lesions appearing on NCCT images, plays an important role in prognostic implications (Barber, et al., *The Lancet* 2000, 355 (9216), 1670-1674; Man, et al., *J. of Neuroimaging* 2014, 25 (2), 263-268; Kim, et al., *J. of Neurology*, 264 (12), 2450-2456). Early detection and segmentation of HMCAS are important in the development of decision support systems for cerebrovascular clinicians.

Quantitative estimation of HMCAS with NCCT is challenging because it manifests as subtle vascular intensity and texture changes. The inter-rater reliability of HMCAS segmentation and classification conducted by experienced radiologists is not usually high (Abul-Kasim, et al., *Neurology India* 2009, 57 (2), 143; Ernst, et al., *Neuroradiology* 2014, 56 (12), 1063-1068). This is mainly due to the low signal-to-noise ratio and low contrast in image of brain tissue. Bone structures, such as the anterior clinoid process, are in close proximity to the middle cerebral artery course, and the co-existing vascular calcifications, common in aging brains, are hard to distinguish from true HMCAS. Besides, the variations of slice thickness and rotated brains further aggravate the difficulty in segmenting the lesions.

Most research on automated NCCT interpretation in ischemic stroke are directed to the detection and segmentation of established infarction (Maldjian, *Amer. of Neuroradiology* 2001, 22 (6), 1050-1055; Qiu, et al., *Radiology* 2020, 294 (3), 638-644; Kuang, et al., *Proc. Int. Conf. Med. Image*

*Comput. Comput. Assist. Intervent*, 2019, 856-863), which has already resulted in the tissue pathologies or death due to inadequate blood supply to the affected region. Previous literature on medical imaging generally adopted traditional image-based solutions, including intensity thresholding, region growing and deformable models. These methods rely heavily on hand-crafted features and have limited feature representation capability. Earlier attempts on NCCT employed traditional unsupervised solutions, such as region growing methods, with pre-defined seeds (Riedel, et al., *Stroke* 2010, 41 (8), 1659-1664) or supervised machine learning classifiers with hand-crafted features (Löber, et al., *Proc. Vis. Comput. Biol. Med. Workshop* 2017, 125-129; Takahashi, et al., *Radiol. Phys. Technol* 2014, 7 (1), 79-88). Löber, et al., (Löber, et al., *Proc. Vis. Comput. Biol. Med. Workshop* 2017, 125-129) extracted possible candidates by thresholding and connected component clustering. Features were then extracted and fed into a random forest classifier for model training. Similarly, Takahashi, et al., (Takahashi, et al., *Radiol. Phys. Technol* 2014, 7 (1), 79-88) proposed to learn a support vector machine classifier with feature vectors obtained through a series of pre-processing steps, including morphologic transformation, false positives reduction and other rule-based schemes.

Recent years have witnessed applications of deep learning in computer vision tasks, particularly in medical image diagnosis (Litjens, et al., *Med. Image Anal.* 2017, 42, 60-88), such as cancer detection (Han, et. al., *JAMA Dermatology* 2020, 156 (1), 29), mutation prediction (Coudray, et al., *Nature Med.* 2018, 24 (10), 1559-1567), and lesion segmentation (Havaei, et al., *Med. Imag. Anal.* 2017, 35, 18-31). In the context of HMCAS assessment, Lisowska's team (Lisowska, et al., *Proc. Annual Conf. Med. Imag. Underst. and Anal.* 2017, 494-505) incorporated the contralateral features and atlas information into the convolutional neural networks (CNN) architecture. However, their work targeted on stroke signs detection and no precise segmentation was performed. Lucas, et al., (Lucas, et al., Proc. *Informatik aktuell Bildverarbeitung für die Medizin* 2019, 74-79) proposed a two-stage neural network to segment and classify clots within the middle cerebral artery and internal carotid artery, but the model's performance was far from satisfactory due to a high false positive rate. Accordingly, the development of systems and/or methods that can enhance the analysis of imaging data, particularly in medical settings, remains an unmet need, and is an area of active research.

Therefore, it is an object of the invention to provide a computer-implemented system and/or method that analyzes data, taking into account variations in two sets of separate input data.

It is also an object of the invention to provide a computer-implemented system and/or method that analyzes imaging data, taking into account variations in two sets of separate input imaging data.

It is a another object of the invention to provide a computer-implemented system and/or method that analyzes medical imaging data, taking into account variations in two sets of separate input medical imaging data.

It is a further object of the invention to provide a computer-implemented system and/or method that analyzes medical imaging data, taking into account variations in two sets of separate input medical imaging data obtained from biological organs that occur in pairs inside a mammal's body.

It is a further object of the invention to provide a computer-implemented system and/or method that analyzes medical imaging data, taking into account variations in two sets of separate input medical imaging data obtained from biological organs that occur inside a mammal's body, and which have bilateral symmetry.

SUMMARY OF THE INVENTION

A computer-implemented system (CIS) and/or a computer-implemented method (CIM) that is not limited to any particular hardware or operating system is provided for processing and/or analyzing medical imaging input data is described. The medical imaging data are non-contrast-enhanced computer tomography (CT) scans. Prior to performing the analysis, the CIS or CIM repositions the imaging data on a stereotaxic coordinate system.

The CIS contains (i) two U-Net architectures with equal weights, which are built on a Siamese architecture (Siamese-U-Net), and (ii) a Dissimilar block operably linked to the two U-Net architectures. The Dissimilar block is built on top of the Siamese-U-Net architecture to form a Dissimilar-Siamese-U-Net architecture (DSU-Net). Within this architecture, the Dissimilar block implements an algorithm that compares variations in features extracted from independent and separate medical imaging data, wherein the features are from corresponding encoding blocks in the two U-Net architectures. The Dissimilar block is further operably linked to the decoding path of each U-Net architecture via skip connections. The skip connections allow the decoding path to further absorb extra inputs derived from the encoding path.

Also described are methods of using the CIS, including, but not limited to, diagnosing a disease or disorder of the brain, such as acute ischemic stroke and/or thromboembolus. A diagnosis of acute ischemic stroke depends on the presence of a hyperdense middle cerebral artery sign. In this setting, the Dissimilar block leverages variations in feature representation between the left and right hemispheres.

DETAILED DESCRIPTION OF THE INVENTION

I. Definitions

Figure 1A:
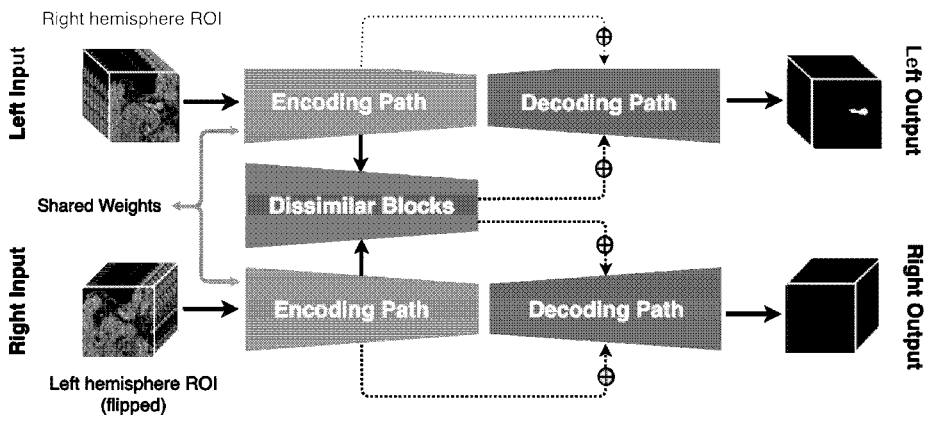
FIGS. 1A, 1B, and 1C are schematics of a non-limiting Dissimilar-Siamese-U-Net (DSU-Net) architecture for the segmentation of the hyperdense middle cerebral artery sign. The Siamese module has dual branches of U-Nets (FIG. 1A). Dissimilar block is built on top of the Siamese-U-Net module that absorbs encoding features from dual branches, transforms into comparison information and passes to the decoding layers (FIG. 1B). A detailed U-Net design is shown in Single Branch U-Net (FIG. 1C).

The term "convolution layer" describes a component in a neural network that transforms data (such as input data) in order to retrieve features from it. In this transformation, the data (such as an image) is convolved using one or more kernels (or one or more filters).

The term "encoding path" refers to a component in a neural network that retrieves, from input data, features of interest (such as volumetric features). It can include multiple levels of resolution to facilitate extraction of features from low to high complexity.

The term "max pooling layer" refers to a component in a neural network, such as a U-Net, located between layers in the encoding path to perform down-sampling for feature compression. "Down-sampling" refers to the process of reducing the dimensions of input data compared to its full resolution, while simultaneously preserving the necessary input information for classification purposes. Typically, coarse representations of the input data (such as image) are generated.

The term "decoding path" refers to a component of a neural network, which mirrors the encoding framework by up-sampling and reconstructing segmentations from coarse to fine resolutions. In "up-sampling," various techniques are utilized to make the dimensions or resolutions of the coarse data progressively closer and/or equal to the dimensions or resolutions of the input image. Up-sampling facilitates drawing conclusions of the data retrieved by the encoding path.

The term "features," as relates to neural networks, refers to variables or attributes in a data set. Generally, a subset of variables is picked that can be used as good predictors by a neural network model. They are independent variables that act like an input in the system. In the context of a neural network, the features would be the input layer, not what are known in the field as the "hidden layer nodes."

A "non-linear function," as relates to activation functions, refers to an activation function in a neural network that can be inserted after a convolution layer, preferably between a convolutional layer and a pooling layer, to introduce non-linearity to the neural network. Activation functions may be used to bound neuron output. As an example, Rectified Linear Unit ("ReLU") can be used.

The term "registration" refers to a spatial transformation that aligns a floating image to a reference coordinate system.

The term "kernel" refers to a surface representation that can be used to represent a desired separation between two or more groups. The kernel is a parameterized representation of a surface in space. It can have many forms, including polynomial, in which the polynomial coefficients are parameters. A kernel can be visualized as a matrix (2D or 3D), with its height and width smaller than the dimensions of the data (such as input image) to be convolved. The kernel slides across the data (such as input image), and a dot product of the kernel and the input data (such as input image) are computed at every spatial position. The length by which the kernel slides is known as the "stride length." Where more than one feature is to be extracted from the data (such as input image), multiple kernels can be used. In such a case, the size of all the kernels are preferably the same. The convolved features of the data (such as input image) are stacked one after the other to create an output so that the number of channels (or feature maps) is equal to the number of kernels used.

The term "segmentation" refers to the process of separating data into distinct groups. Typically, data in each group are similar of each other and different from data in other groups. In the context of images, segmentation involves identifying parts of the image and understanding to what object they belong. Segmentation can form the basis for performing object detection and classification. For an image of a biological organ, for example, segmentation can mean identifying the background, organ, parts of the organ, and instruction (where present).

The term "skip connections" are extra connections between nodes in different layers of a neural network that skip one or more layers of nonlinear processing.

II. Computer-Implemented Systems and Methods i. Computer-Implemented System

A computer-implemented system (CIS) that is not limited to any particular hardware or operating system is provided for processing and/or analyzing imaging and/or non-imaging input data is described. The CIS allows a user to make diagnoses or prognoses of a disease and/or disorder, based on output preferably displayed on a graphical user interface. A preferred disease and/or disorder includes acute ischemic stroke or thromboembolus.

The CIS contains (i) preferably two segmentation architectures independently containing neural networks, and (ii) a Dissimilar block operably linked to the herein preferred two segmentation architectures. Preferably, the Dissimilar block contains a tool (such as an algorithm) that compares features in data from corresponding blocks in the two or more segmentation architectures.

In some forms, the neural networks have shared weights. Preferably, the shared weights are equal. Preferably, data from two different biological sources are provided to the neural networks in the herein preferred two segmentation architectures, such that each segmentation architecture receives a separate and independent set of input data. In some forms, the neural networks are independently U-net neural networks. Preferably, the neural networks are 3D U-net neural networks.

After receiving the separate and independent input data, preferably, the CIS includes a pre-processing registration layer that involves repositioning the images on a common frame of reference, such as a stereotaxic coordinate system. Preferably, the input data are imaging data. More preferably, the input imaging data are from medical imaging applications, including, but not limited to, computed tomography (CT) scans, X-ray images, magnetic resonance images, ultrasound images, positron emission tomography images, magnetic resonance angiograms, and combinations thereof.

The Dissimilar block assesses discrepancies in feature representations, at different degrees of complexity, extracted from the separate and independent input data.

In some forms, the neural networks independently contain an encoding path, a decoding path, or both. Preferably, the neural networks independently contain an encoding path and a decoding path.

In some forms, the encoding path and the decoding path are connected via the Dissimilar block through one or more skip connections, preferably wherein, the Dissimilar block receives encoding features from encoding paths in the neural networks, transforms the encoding features into comparison information and passes that decoding paths in the neural networks. Preferably, the Dissimilar block connects corresponding encoding blocks within the encoding paths of the herein preferred two segmentation architectures. In some forms, the Dissimilar block also connects to the series of decoding blocks via a skip connection.

In some forms, the encoding path contains a series of encoding blocks. In some forms, the encoding path contains between 2 and 15 encoding blocks, inclusive, between 2 and 10 encoding blocks, inclusive, between 2 and 9 encoding blocks, inclusive, between 2 and 8 encoding blocks, inclusive, between 4 and 10 encoding blocks, inclusive, between 5 and 10 encoding blocks, inclusive. In some forms, the encoding path contains 2, 3, 4, 5, 6, 7, 8, 9, 10, 11, 12, 13, 14, or 15 encoding blocks. In some forms, the encoding path contains 6 encoding blocks.

In some forms, the encoding blocks independently contain one or more convolution layers, activation function layers, max pooling layers, or a combination thereof. Preferably, the one or more activation function layers compress a range of output from the one or more convolution layers. In some forms, at least one of the one or more activation function layers contains a non-linear function.

In some forms, the encoding blocks independently contain (i) two or more consecutive convolution layers, followed by (ii) one or more activation function layers, followed by (iii) one or more max pooling layers. Preferably, each convolution layer in the two or more consecutive convolution layers is followed by one or more activation function layers.

In some forms, the encoding blocks independently contain (i) two consecutive convolution layers, each followed by (ii) one activation function layer, followed by (iii) one or more max pooling layers.

In some forms, the one or more max pooling layers have a stride size of two for down sampling.

In some forms, at least one of the encoding blocks has one max pooling layer. In some forms, each of the encoding blocks has one max pooling layer, except the last encoding block in the series of encoding blocks.

In some forms, the decoding path contains a series of decoding blocks. In some forms, the decoding blocks independently contain one or more up-sampling layers, concatenation layers, convolutional layers, activation function layers, or a combination thereof.

In some forms, the decoding blocks independently contain (i) one or more up-sampling layers, followed by (ii) one or more concatenation layers, followed by (iii) two or more consecutive convolutional layers, followed by (iv) one or more activation function layers.

In some forms, the decoding wherein the decoding blocks independently contain (i) one up-sampling layer, followed by (ii) one concatenation layer, followed by (iii) two consecutive convolutional layers, followed by (iv) one or more activation function layers.

Preferably, each convolution layer in the two or more consecutive convolutional layers is followed by one or more activation function layers.

In some forms, the one or more activation function layers in the encoding blocks, decoding blocks, or both, are independently a one of the one or more activation function layers are a parametric rectified linear unit activation function (PReLu) layer, a rectified linear unit activation function (ReLu) layer, or a sigmoid activation function layer. Preferably, the activation function layer is a PReLu. In some forms, the activation function layer is a PReLu in each of the encoding blocks, except in the last encoding block in the series of encoding blocks, in which the activation function layer is preferably a sigmoid function.

In a particularly preferred form, the CIS has two image segmentation architectures, built on a Siamese framework forming a Siamese-U-Net. Further, each of the two segmentation architectures contains U-Net neural networks that are 3D U-Nets. The U-Net performs image segmentation in medical imaging applications (Litjens, et al., *Med. Image Anal.* 2017, 42, 60-88; Christ, et al., *Proc. Int. Conf. Med. Image Comput. Comput. Assist. Intervent.* 2016, 415-423; Falk, et al., *Nature* Methods 2019, 16 (1), 67-70). The U-net neural networks contain an encoding path and a decoding path, containing a series of encoding blocks and a series of decoding blocks, respectively. The encoding path extracts a hierarchy of image features from low to high complexity, while the decoding path transforms the features and reconstructs the segmentation maps from coarse to fine resolution. This CIS further contains a Dissimilar block built on top of the Siamese-U-Net. The Dissimilar block connects corresponding encoding blocks in encoding blocks of the encoding paths. The encoding blocks contain two or more consecutive convolution layers, wherein the last convolution layers in a down-sampling arm of at least one of the U-net neural networks connect with one or more sigmoid activation function layers, and the other consecutive convolution layers connect with one or more PReLU activation function layers. The last convolution layers in the down-sampling arm of the U-net neural networks utilize kernels of size 1×1×1, and wherein other consecutive convolution layers utilize 3D kernels of size 3×3×3. The decoding blocks contain one or more up-sampling layers that utilize bilinear interpolation with a stride size of two. Further, the decoding blocks contain a concatenation layer connected to the one or more up-sampling layers and the Dissimilar block preferably via a skip connection. The specially designed skip connections allow the decoding path to further absorb the extra inputs derived from the encoding path.

ii. Computer-Implemented Methods

Also described is a computer-implemented method (CIM) for analyzing data, which involves using any of the CISs described above. Preferably, the CIM involves visualizing on a graphical user interface, output from these CISs. Visualizing this output facilitates the diagnosis, prognosis, or both, of a disease or disorder in a subject. The disease or disorder includes, but is not limited to, acute ischemic stroke, thromboembolus, tumors (such as brain, breast, cancer, etc), cysts, joint abnormalities, abdominal diseases, liver diseases, kidney disorders, neuronal disorders, or lung disorders.

In some forms, the data are images from one or more biological samples. Preferably, prior to analyzing the images, the images are repositioned into a reference coordinate system. In some forms, the coordinate system is a stereotaxic coordinate system. As discussed above, the input imaging data are preferably from medical imaging applications, including, but not limited to, computed tomography (CT) scans, X-ray images, magnetic resonance images, ultrasound images, positron emission tomography images, magnetic resonance angiograms, and combinations thereof. In some forms, the images are non-contrast-enhanced CT scans. Preferably, the images are internal body parts of a mammal. In some forms, the internal body parts are brains, blood vessels, hearts, stomachs, livers, prostates, testes, breasts, ovaries, kidneys, neurons, bones, or lungs.

Preferably, the images are provided from two biological organs that occur in pairs in a mammal, or from separate segments of a biological organ that has bilateral symmetry. In some forms, the organ that has bilateral symmetry is a brain, and the segments are the left and right hemispheres of the brain. In these forms, the disease of interest can be acute ischemic stroke or thromboembolus, diagnosed by analyzing an image containing a middle cerebral artery.

III. Methods of Using

The described CIS or CIM can be utilized to analyze data. The CIS or CIM is one of general applicability and is not limited to imaging data from a patient population in a specific geographical region of the world. Preferably, the data are imaging data, such as medical imaging data obtained using well-known medical imaging tools such as computed tomography (CT) scans, X-ray images, magnetic resonance images, ultrasound images, positron emission tomography images, magnetic resonance angiograms, and combinations thereof. Within the context of medical imaging, the CIS or CIM can be employed in the diagnosis or prognosis of diseases or disorders.

The disclosed CISs and CIMs can be further understood through the following enumerated paragraphs or embodiments.

1. A computer-implemented system (CIS) containing:
(i) two segmentation architectures independently containing neural networks, and
(ii) a Dissimilar block operably linked to the two segmentation architectures, wherein the Dissimilar block comprises a tool that compares features in data from corresponding blocks in the two segmentation architectures.

2. The CIS of paragraph 1, wherein the neural networks have shared weights, preferably equal shared weights.

3. The CIS of paragraph 1 or 2, wherein neural networks independently contain image segmentation architectures.

4. The CIS of any one of paragraphs 1 to 3, wherein the neural networks independently contain an encoding path, a decoding path, or both.

5. The CIS of any one of paragraphs 1 to 4, wherein the neural networks independently contain an encoding path and a decoding path.

6. The CIS of paragraph 5, wherein the encoding path and the decoding path are connected via the Dissimilar block through one or more skip connections, preferably wherein, the Dissimilar block receives encoding features from encoding paths in the neural networks, transforms the encoding features into comparison information and passes that decoding paths in the neural networks.

7. The CIS of any one of paragraphs 4 to 6, wherein the encoding path contains a series of encoding blocks.

8. The CIS of paragraph 7, wherein the encoding blocks independently contain one or more convolution layers, activation function layers, max pooling layers, or a combination thereof.

9. The CIS of paragraph 8, wherein the one or more activation function layers compress a range of output from the one or more convolution layers.

10. The CIS of paragraph 8 or 9, wherein at least one of the one or more activation function layers contains a non-linear function.

11. The CIS of any one of paragraphs 7 to 10, wherein the encoding blocks independently contain (i) two or more consecutive convolution layers, followed by (ii) one or more activation function layers, followed by (iii) one or more max pooling layers.

12. The CIS of any one of paragraphs 7 to 11, wherein the encoding blocks independently contain (i) two consecutive convolution layers, each followed by (ii) one activation function layer, followed by (iii) one or more max pooling layers.

13. The CIS of paragraph 11 or 12, wherein each convolution layer in the two or more consecutive convolution layers is followed by one or more activation function layers.

14. The CIS of paragraph 13, wherein at least one encoding block has one max pooling layer.

15. The CIS of any one of paragraphs 8 to 14, wherein the one or more max pooling layers have a stride size of two for down-sampling.

16. The CIS of any one of paragraphs 4 to 15, wherein the decoding path contains a series of decoding blocks.

17. The CIS of paragraph 16, wherein the decoding blocks independently contain one or more up-sampling layers, concatenation layers, convolutional layers, activation function layers, or a combination thereof.

18. The CIS of paragraph 16 or 17, wherein the decoding blocks independently contain (i) one or more up-sampling layers, followed by (ii) one or more concatenation layers, followed by (iii) two or more consecutive convolutional layers, followed by (iv) one or more activation function layers.

19. The CIS of any one of paragraphs 16 to 18, wherein the decoding blocks independently contain (i) one up-sampling layer, followed by (ii) one concatenation layer, followed by (iii) two consecutive convolutional layers, followed by (iv) one or more activation function layers.

20. The CIS of paragraph 18 or 19, wherein each convolution layer in the two or more consecutive convolutional layers is followed by one or more activation function layers.

21. The CIS of any one of paragraphs 8 to 20, wherein one of the one or more activation function layers are a parametric rectified linear unit activation function (PReLu) layer, a rectified linear unit activation function (ReLu) layer, or a sigmoid activation function layer.

22. The CIS of any one of paragraphs 8 to 21, wherein the activation function layer is a PReLu.

23. The CIS of any one of paragraphs 7 to 22, wherein the Dissimilar block connects corresponding encoding blocks within the encoding paths of the two or more segmentation architectures.

24. The CIS of any one of paragraphs 1 to 23, wherein the neural networks are independently U-net neural networks (such as 3D-Unet).

25. The CIS of any one of paragraphs 1 to 24, having the two segmentation architectures on a Siamese framework.

26. The CIS of paragraph 25, wherein the neural networks contain 3D-Unet neural networks.

27. The CIS of paragraph 26, wherein the 3D-Unet neural networks independently contain a series of encoding blocks, wherein the encoding blocks comprise two or more consecutive convolution layers, wherein the last convolution layers in a down-sampling arm of at least one of the 3D-Unet neural networks connect with one or more sigmoid activation function layers.

28. The CIS of paragraph 27, wherein the 3D-Unet neural networks independently contain a series of decoding blocks comprising one or more up-sampling layers that utilize bilinear interpolation with a stride size of two.

29. The CIS of paragraph 28, wherein the decoding blocks contain a concatenation layer connected to the one or more up-sampling layers and the Dissimilar block preferably via a skip connection.

30. The CIS of any one of paragraphs 27 to 29, wherein the last convolution layers in the down-sampling arm of the 3D-Unet neural networks utilize kernels of size 1×1×1, and wherein other consecutive convolution layers utilize 3D kernels of size 3×3×3.

31. The CIS of any one of paragraphs 27 to 30, wherein the other consecutive convolution layers connect with one or more PReLU activation function layers.

32. A computer-implemented method (CIM) for analyzing data, the CIM involving:

(a) visualizing on a graphical user interface, output from the CIS of any one of paragraphs 1 to 31.

33. The CIM of paragraph 32, wherein visualizing the output on the graphical user interface, provides a diagnosis, prognosis, or both, of a disease or disorder in a subject.

34. The CIM of paragraph 32 or 33, wherein the data are images of one or more biological samples.

35. The CIM of any one of paragraphs 32 to 34, wherein the data are images of internal body parts of a mammal.

36. The CIM of any one of paragraphs 32 to 35, wherein the data are images from brains, blood vessels, hearts, stomachs, livers, prostates, testes, breasts, ovaries, kidneys, neurons, bones, or lungs.

37. The CIM of any one of paragraphs 32 to 36, wherein the CIM involves providing to the CIS, prior to step (a), images from two segments of a biological organ.

38. The CIM of any one of paragraphs 32 to 37, wherein the CIM involves providing to the CIS, prior to step (a), images are from two biological organs that occur in pairs in a mammal, or from separate segments of a biological organ that has bilateral symmetry.

39. The CIM of paragraph 37 or 38, further involving repositioning the images into a reference coordinate system.

40. The CIM of paragraph 39, wherein the reference coordinate system is a stereotaxic coordinate system.

41. The CIM of any one of paragraphs 32 to 40, wherein the data are selected from the group consisting of computed tomography (CT) scans, X-ray images, magnetic resonance images, ultrasound images, positron emission tomography images, magnetic resonance angiograms, and combinations thereof.

42. The CIM of paragraph 41, wherein the CT scans are non-contrast-enhanced CT scans.

43. The CIM of any one of paragraphs 33 to 42, wherein the disease or disorder is acute ischemic stroke, thromboembolus, tumors (such as brain, breast, cancer, etc), cysts, joint abnormalities, abdominal diseases, liver diseases, kidney disorders, neuronal disorders, or lung disorders.

44. The CIM of paragraph 43, wherein the two segments are the left and right hemispheres of a brain.

45. The CIM of any one of paragraphs 33 to 44, wherein the disease or disorder is acute ischemic stroke or thromboembolus.

46. The CIM of any one of paragraphs 32 to 45, wherein the output contains an image containing a middle cerebral artery.

EXAMPLES

Example 1: 3D Dissimilar-Siamese-U-Net for Hyperdense Middle Cerebral Artery Sign Segmentation The neural networks described herein were designed by collaborating with several experienced cerebrovascular specialists, by observing the process of how they read/analyzed CT scans. To identify hyperdense middle cerebral artery sign (HMCAS), specialists routinely assessed the appearance discrepancy between left and right hemispheres. Because, in most situations, the occurrence of a stroke is mainly within the unilateral hemisphere, and such abnormality can result in a change of Hounsfield Unit (HU) intensities within the onset hemisphere. The loss of gray-white differentiation is a significant early CT sign of cerebral ischemia, due to an increase in the relative water concentration within the ischemic tissues after symptom onset (Tomura, et al., *Radiology* 1988, 168 (2), 463-467; von Kummer, et. al., *Amer. J. of Neuroradiology* 1994, 15 (1), 9-15; Truwit, et al., *Radiology* 1990, 176 (3), 801-806). Therefore, comparisons between bilateral hemispheres substantially assist in discriminating between subtle changes in the affected and the normal brain tissue.

Bilateral symmetry often appears in parts of the body, such as the brain, chest, and bone etc. As for a developing lesion, asymmetry gradually appears due to differentiation of perfusion, blood supply, and metabolism beyond normal tissues. Recent computer-aided diagnostic systems have witnessed the development of symmetry technique that has gradually become a commonly used feature in detecting pathologies and has widely been applied for medical image segmentation such as brain tumors (Saddique, et al., *Comput. and Math. Methods in Med.* 2014, 2014, 1-10), prostate cancer (Litjens, et al., *IEEE Trans. Med. Imag.* 2015, 33 (5), 1083-1092), and breast cancer (Kooi and Karssemeijer, *J. of Med. Imag.* 2017, 4 (04), 1). Typically, an additional registration step helps to reposition the images into a stereotaxic coordinate system, and comparisons between bilateral hemispheres on the registered images can be made by extracting features from bilateral tissues which are then combined and fed into a machine learning algorithm. However, no deep learning framework adopts such comparison for stroke sign segmentation.

To alleviate this issue, an end-to-end system has been developed, including a specially designed pipeline for head NCCT pre-processing and a fully automated deep neural network called Dissimilar-Siamese-U-Net (DSU-Net). The DSU-Net originated based on the incorporation of the Siamese framework (Koch, et al., *Int. Conf. Mach. Learn. Deep Learn. Workshop* 2015) and the U-Net design (Ronneberger, et al., *Proc. Int. Conf. Med. Image Comput. Comput. Assist. Intervent.* 2015, 234-241). On one hand, the proposed system allows separate inputs from the two hemispheres; on the other hand, it further explores the feature representation of the discrepancies between the bilateral input pairs.

The Siamese framework was designed, preferably to use two U-Nets as twin sub-networks with shared weights. For any input pairs of image volumes, high-level features are extracted through a series of convolution and pooling operations. The dedicatedly designed Dissimilar block allows the decoding path to further absorb the extra information derived from two encoding branches.

Materials and Methods i. Data Pre-Processing

The HMCAS usually occurs within the sylvian fissure, which is posterior to the lesser wings of sphenoid bone. Hence, the proposed automated pre-processing pipeline extracts the specific region of interest (ROI) before feeding into the deep learning model. Since the brain orientations in the NCCT scans varied in their positions and shapes, all brains were registered to a pre-defined atlas so that the brain structures could be geometrically aligned. Then the ROI within the atlas could be adapted to the registered brains as well.

The pre-defined atlas volume was obtained by taking an average of CT brain images from all the patients. The template had 0.4 mm×0.4 mm resolutions and 0.5 mm thickness with length, width and height of 512, 512 and 288 voxel units, respectively. The registration was able to input raw brain CT scans with various resolutions and thicknesses; while the output brains all had uniform spacing parameters and dimensionality that were identical to the atlas.

The pre-processing pipeline of the ROI extraction preferably has three main steps. The first step involves extracting the brain and removing skulls from brain CT images by using a skull stripping method. The method proposed by Muschelli's team (Muschelli, et al., Neuroimage 2015, 114, 375-385) was adopted, and the implementation was conducted using the FMRIB Software Library Brain Extraction Tool (FSL-BET) (Smith, et al., NeuroImage 2004, 23 Suppl. 1, S208-219; Jenkinson, NeuroImage 2012, 62 (2), 782-790). Secondly, a 3D affine transformation was applied to geometrically align the skull-stripped brain to the pre-defined atlas using FMRIB's linear image registration tool (FLIRT) (Smith, et al., NeuroImage 2004, 23 Suppl. 1, S208-219; Jenkinson, NeuroImage 2012, 62 (2), 782-790) based on a mutual information cost function. Thirdly, a 3D bounding box enclosing the proximal HMCAS was used to extract the ROI. In an attempt to fully cover the region in which HMCAS could potentially occur, the collaborating cerebrovascular specialists drew the bounding box on the atlas and then generalized to all registered brains. The bounding box had size of 256×128×96 voxels, and were then split into two symmetric boxes by the midsagittal plane, each with size 128×128×96 voxels. In order to compare both bounding boxes in the left and right hemispheres, the one in the left hemisphere was flipped on the axial plane so that the two bounding boxes were aligned. Finally, after thresholding the HU between the 2.5% and 97.5% quantile range, normalization was implemented based on each bounding box.

ii. Siamese-U-Net

The Siamese-U-Net framework has two identical U-Nets as twin sub-networks with shared weights in the encoding path, FIG. 1A. The U-Net design belongs to the category of fully convolutional network (FCN) (Long, et al., *Proc. IEEE Conf. Comput. Vis. Pattern Recognit.* 2015, 3431-3440), which performs a voxel-wise classification and essentially serves as a filter that projects the input CT volume to a probability map, where each element represents the likelihood that the corresponding input voxel belongs to HMCAS. There are two separate input channels for patches selected symmetrically from the left and right hemispheres. The input pairs pass through a sequence of encoding blocks formed with convolution and pooling operations. The encoding path extracts a hierarchy of volumetric features from low to high complexity. The decoding path mirrors the encoding framework by up-sampling and reconstructing the segmentations from coarse to fine resolutions. In addition, the employment of skip-connections from shallow to deeper layers incorporated both the local and global information to obtain more refined segmentation results.

Figure 1B:
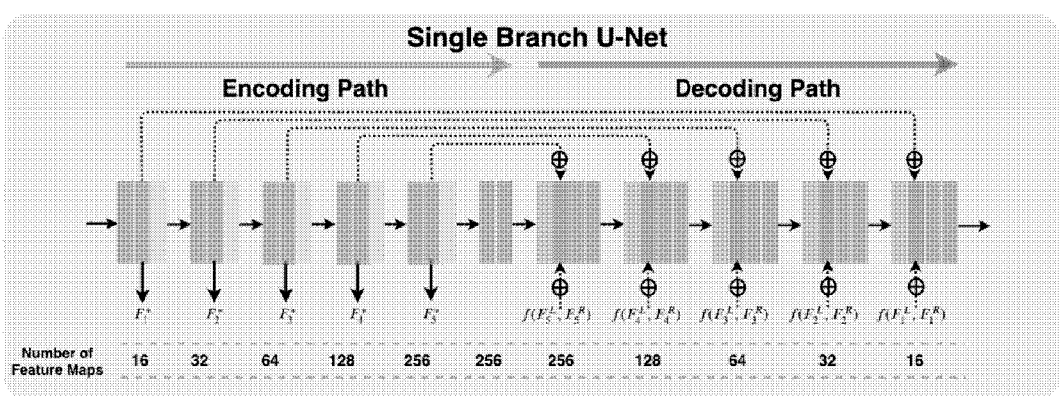

The paired input volumes have identical size (128×128×96). The encoding path had six encoding blocks that expand the number of feature maps from 16 to 256, FIG. 1B. Each encoding block contained consecutive convolution operations and Parametric ReLU (He, et al., Proc. IEEE *Int. Conf. Comput. Vis.* 2015, 1026-1034), followed by a max pooling layer with a stride size of 2 for down-sampling. The decoding path had a series of decoding blocks, which started from up-sampling layers using bilinear interpolation with a stride size of 2, and were then concatenated with other two sources from the encoding blocks and Dissimilar block, followed by two consecutive convolutional layers and activation functions of Parametric ReLU. All convolution layers utilized 3D kernels with size 3×3×3, except the last convolution layers within the bottom of both sub-networks that used a kernel size of 1×1×1 and connected with sigmoid activation functions.

iii. Dissimilar Block

Figure 1C:
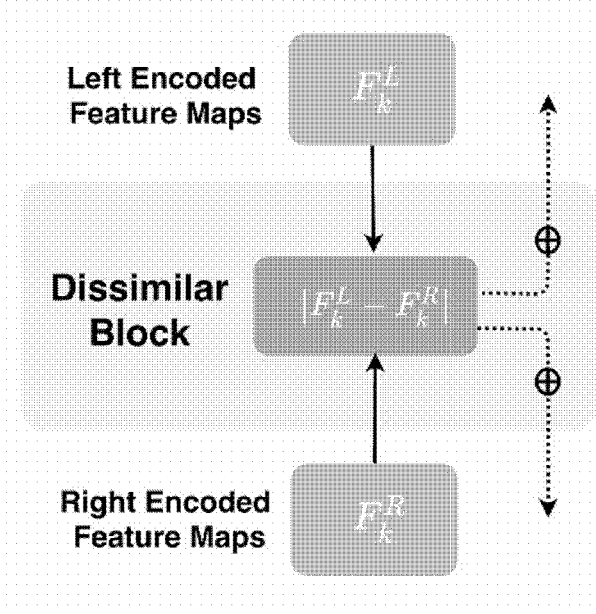

As shown in FIGS. 1A and 1C, the Dissimilar block was built on top of the Siamese-U-Net and worked as a transformation block connecting the corresponding encoding blocks within the two U-Net branches. The Dissimilar block explored the feature representation of the discrepancies between the left and right hemispheres, FIG. 1C, at different complexity stages, thereby improving segmentation performance by concatenating such informative features to the decoding path with such extra information. The feature map generated by the Dissimilar block is given by:

$$f(F_k^L, F_k^R) = |F_k^L - F_k^R| \qquad (1)$$

where the $$F_k^L \text{ and } F_k^R$$

are the k-th encoded feature maps derived from CT volumes in the left and right sub-networks, respectively, i.e., the sub-networks receiving data from the left and right hemispheres, respectively. The f(.) represents the element-wise absolute difference between the $$F_k^L \text{ and } F_k^R$$

feature maps. Based on Eq. (1) a patient with a healthy brain would output dissimilar features close to zeros since no significant difference exists between the input pairs of data. On the contrary, if a patient experienced HMCAS, the tissues within the onset hemisphere would become darker than the contralateral one. Such pathological variations would lower the HU intensities, resulting in output dissimilar features greater than zero.

iv. Loss Function

Due to the extremely small size of HMCAS, the number of lesion voxels is much less than that of non-lesion ones. Such data imbalance problems frequently result in biased model performance with high precision but low recall, which is undesired especially in medical applications where false negatives are much less tolerable than false positives. To tackle this problem, Tversky loss (Salehi, et al., *Mach. Learning in Med. Imag. Workshop* 2017, 379-387) was implemented.

The Tversky loss is a generalized Dice loss, which is derived from a dice similarity coefficient (DSC). The DSC is a measure of overlap of the predicted mask (P) and the ground truth (G) of the lesion. Mathematically, it is defined as:

$$DSC = \frac{2|P \cap G|}{|P| + |G|} = \frac{|P \cap G|}{|P \cap G| + 0.5|P \cap \overline{G}| + 0.5|\overline{P} \cap G|} \qquad (2)$$

where $\overline{P}$ and $\overline{G}$ are, respectively, the regions outside the predicted mask and the ground truth. $|P \cap G|$, $|P \cap \overline{G}|$, and $|\overline{P} \cap G|$ are the number of pixels classified as true positive (TP), false positive (FP), and false negative (FN), respectively. The DSC is a special case of Tversky index (TI), treating FP and FN as being equally weighted.

As shown in Eq. (2), TI generalizes DSC by involving two tuning parameters, $\alpha$ and $\beta$, to control the weighting of FP and FN:

$$DSC = \frac{|P \cap G|}{|P \cap G| + \alpha|P \cap \overline{G}| + \beta|\overline{P} \cap G|}. \qquad (3)$$

Typically, the Tversky loss is set as:

$$TL = 1 - TI. \qquad (4)$$

Given that the exemplified model contains two sub-networks for the two hemispheres, the overall loss is the average of the Tversky losses from the two sub-networks:

$$L = \frac{(TL_L + TL_R)}{2}, \qquad (5)$$

where $TL_L$ and $TL_R$ are the Tversky losses for the left and right hemispheres, respectively.

v. Experiments

The following section describes the study population, ground truth protocol, data partition, and other implementation details including the execution environment, the configuration of training parameters, and model evaluation metrics. Ablation studies were conducted in order to illustrate the effectiveness of the proposed modules. To demonstrate the superiority of the system, comparative experiments were conducted with several state-of-the-art segmentation models. Moreover, radiologists' inter-rater reliability was used to validate the stable performance of the proposed system.

A. Study Population and Data Acquisition

The study subjects were retrospectively collected from the clinical management systems established by Hong Kong Hospital Authority. Data recorded within the clinical management systems were obtained from patients admitted to all public hospitals within the territory-wide region of Hong Kong. The study population used in this research was collected in two stages.

The first stage included 300 potential acute ischemic stroke patients based on a disproportionate random sampling scheme in 2016 (Tsang, et al., *Int. J. of Stroke* 2019, 15 (1), 69-74; You, et al., *Frontiers in Neuroinformatics* 2020, 14, 13). Patients (a) 18 years or older; (b) having a principal diagnosis of cerebral embolism with mention of cerebral infarction or cerebral artery occlusion unspecified with mention of cerebral infarction; (c) admitted via Accident and Emergency (A&E) services; and (d) with head CT scans performed within 24 hours of the admission, were included in the study. The second stage collected another 324 patients between January 2016 and June 2018. Besides the inclusion criteria from (a) to (d), all subjects within the second stage were required to have both head CT exam, performed within 12 hours of A&E admission, and follow-up CT angiography exam, conducted within 3 hours after the plain CT exam.

B. Empirical Experiments

I. Data

The slice intervals of the CT scans ranged from 0.4 to 5.0 mm, and around two-thirds of them were 5-mm thick-cut scans. The pixel spacings ranged between 0.39 mm/pixel and 0.50 mm/pixel with a median of 0.42 mm/pixel. All scans had identical matrix size of 512×512 pixels on the axial plane. The segmentation annotations were independently evaluated by multiple clinical cerebrovascular specialists. Besides brain NCCT, patients' follow-up CT angiogram and discharge reports were used in the final consensus stage for generating the ground truth labels. The labels were manually drawn with FMRIB Software Library (FSL) (Smith, et al., NeuroImage 2004, 23 Suppl. 1, S208-219; Jenkinson, NeuroImage 2012, 62 (2), 782-790). Among the total 624 subjects, HMCAS was observed in 195 NCCT. For thick-cut scans (5 mm), HMCAS showed on only 1 or 2 slices; while for thin-cut scans (0.5 mm-1 mm), the HMCAS usually could be observed within 5 to 15 slices.

The total of 624 patients were randomly split into 80% for model training, 10% for validation and 10% for testing. This procedure was repeated 10 times and all the evaluation measurements were averaged to obtain the final results along with their corresponding standard deviations.

II. Negative Mining Scheme for Model Training

Negative mining technique (Dong, et al., *Proc. IEEE Conf. Comput. Vis. Pattern Recognit.* 2017, 1851-1860) was adopted to address the data imbalance problem in HMCAS segmentation. On one hand, all 3D images for patients with HMCAS were retained in the training samples. On the other hand, a random sample was drawn from the non-lesion group at the beginning of each epoch. The ratio for training subjects with and without HMCAS was set as 2:1. The negative mining technique allowed the model to learn HMCAS with an adequate number of lesion samples and non-lesion samples within each epoch to train the proposed model.

III. Parameters Setting

The model was parameterized using Adam optimizer with initial learning rate 1e-5, which was updated by multiplying by 0.9 if no improvement observed on validation DSC within 20 epochs. The maximum epoch was 250 and the batch size was 8. Parameters a and within the Tversky loss were set as 0.7 and 0.3. Our experiments were implemented in Python with TensorFlow and Keras libraries on a Tesla V100 GPU card.

C. Evaluation Metrics

The model performance was evaluated through both overlap-based methods, such as Dice similarity score (DSC), precision and recall, and surface-based methods, e.g. average symmetric surface distance (ASSD) and maximum symmetric surface distance (MSD). Given predicted binary segmentations (P) and ground truth mask (G), these metrics can be formulated as follows.

$$DSC(P, G) = \frac{2|P \cap G|}{|P| + |G|} = \frac{TP}{2TP + FP + FN} \quad (6)$$

$$\text{Jaccard}(P, G) = \frac{|P \cap G|}{|P \cup G|} = \frac{TP}{TP + FP + FN} \quad (7)$$

$$\text{Precision}(P, G) = \frac{|P \cap G|}{|P|} = \frac{TP}{TP + FP} \quad (8)$$

$$\text{Recall}(P, G) = \frac{|P \cap G|}{|G|} = \frac{TP}{TP + FN} \quad (9)$$

where TP, FP and FN represent the numbers of true positives, false positives and false negatives, respectively.

Surface distance metrics are a set of correlated measures of the distance between the surfaces of a reference and predicted lesion. Let S(P) denote the set of surface voxels of P. The shortest distance of an arbitrary voxel v to S(P)) is defined as:

$$d(v, S(P)) = \min_{SP \in S(P)} \|v - S_p\| \quad (10)$$

where $\|*\|$ denotes the Euclidean distance.

The ASSD is then given by:

$$ASSD(P, G) = \frac{1}{|S(P)| + |S(G)|} \left( \sum_{SP \in S(P)} d(S_p, S(G)) + \sum_{SG \in S(G)} d(S_G, S(P)) \right). \quad (11)$$

The MSD is similar to ASSD except that the maximum distance is taken instead of the average. Both the ASSD and MSD were calculated based on units of pixels. The MSD is given as:

$$MSD(P, G) = \max \begin{cases} \max_{SP \in S(P)} d(S_p, S(G)), \\ \max_{SG \in S(G)} d(S_G, S(P)) \end{cases} \quad (12)$$

All these assessment metrics were calculated on a per patient basis, and the results were obtained by averaging all patients in the testing cohort. For overlap-based measurements—DSC, precision and recall, if a patient had both segmented mask and ground truth empty, the metrics would be ones. If either segmented mask or ground truth was empty, and the other one was not empty, the metrics would be zeros. For surface-based metrics, ASSD and MSD, if any one of segmented mask and ground truth was empty, they would become zeros and only non-zero cases would be reported.

D. Ablation and Comparative Studies

Ablation studies were carried out to evaluate the performance of various components of DSU-Net. Multiple experimental designs were conducted aiming to investigate the influence of the 3D framework, Siamese architecture and Dissimilar block. To compare the 2D and 3D designs, all 2D models were constructed to match with the design setting of the 3D models, including the number of channels, and the depth of encoding and decoding paths. Moreover, their inputs and kernels were adjusted to cater for the 2D slices. The Siamese module was probed by comparing it with a 2D/3D U-Net on the whole brain by combining the two separated hemispheres so that the input of the U-Net model was a single slice or volume. For example, two 3D input volumes each with size 128×128×96 voxels would be converted into one sizing in 256×128×96 voxels. Finally, the ablation study for the Dissimilar block involved comparing the performances of DSU-Net and Siamese-U-Net since the Dissimilar block is built on top of the Siamese-U-Net.

To illustrate the superiority of the DSU-Net, several state-of-the-art segmentation models were trained and compared, namely SegNet (Badrinarayanan, et al., *IEEE trans. Pattern Anal. Mach. Intell.* 2017, 39 (12), 2481-2495), PSP-Net (Zhao, et al., Proc. *IEEE Conf. Comput. Vis. Pattern Recognit.* 2017, 2881-2890), DeepLabV3 (Chen, et al., *Proc. Euro. Conf. Comput. Vis.* 2018, 801-818) and UNet++(Zhou, et al., *Deep Learn. Med. Imag. Anal. Workshop* 2018, 3-11). As these methods are all 2D-based approaches, the inputs of these models were 2D slices that combined the left and right ROIs (each with size 128×128 pixels) into a whole (size in 256×128 pixels). Relevant parameters settings for these methods were modified accordingly.

E. Tversky Loss Function

As stated earlier, the volumes of HMCAS are extremely small, such that non-HMCAS voxels account for a large percentage even after the pre-processing steps. According to Eq. 3, the Tversky loss introduced two hyperparameters, $\alpha$ and $\beta$, to put different emphasis on false positive and false negative predictions, thereby alleviating such data imbalance issues. Experiments were set up to investigate the effectiveness of Tversky loss by using different combinations of $\alpha$ and $\beta$. The choices of $\alpha$ ranged from 0.5 to 0.9 with step of 0.1 while R was set to be $1-\alpha$ that decreased from 0.5 to 0.1.

Results

There were 624 patients involved in the current study, among which 300 were females and 324 were males. The median age the study subjects was 72 years (IQR: 61-83). The HMCAS was detected in 195 (31.25%) patients. The HMCAS had a mean volume of 211.31 mm$^3$ ($\pm$standard deviation of 160.32 mm$^3$) and a mean Hounsfield Unit (HU) of 40.15 ($\pm$standard deviation of 6.08) on a per patient basis.

Figure 2A:
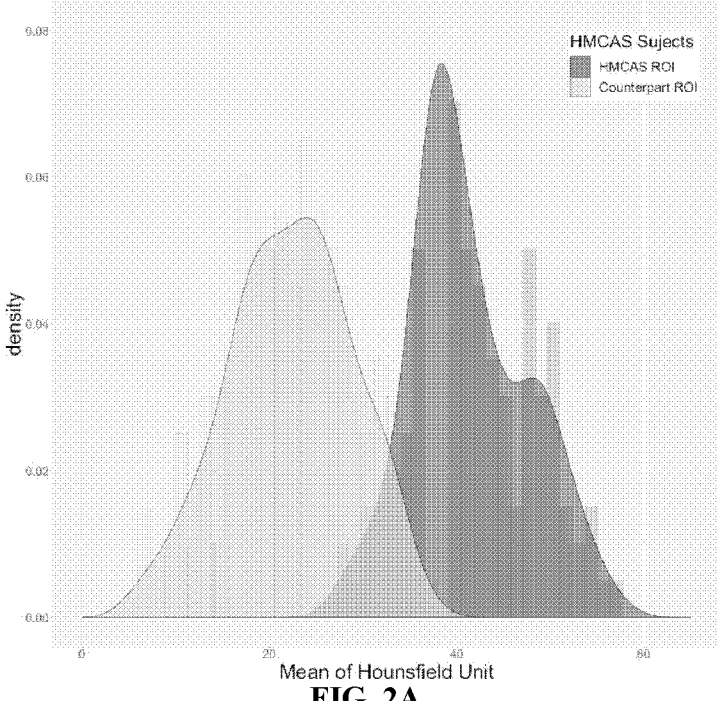
FIGS. 2A and 2B are histograms showing mean Hounsfield Unit values of symmetric regions of interest within HMCAS subjects (FIG. 2A) and non-HMCAS subjects (FIG. 2B).
Figure 2B:
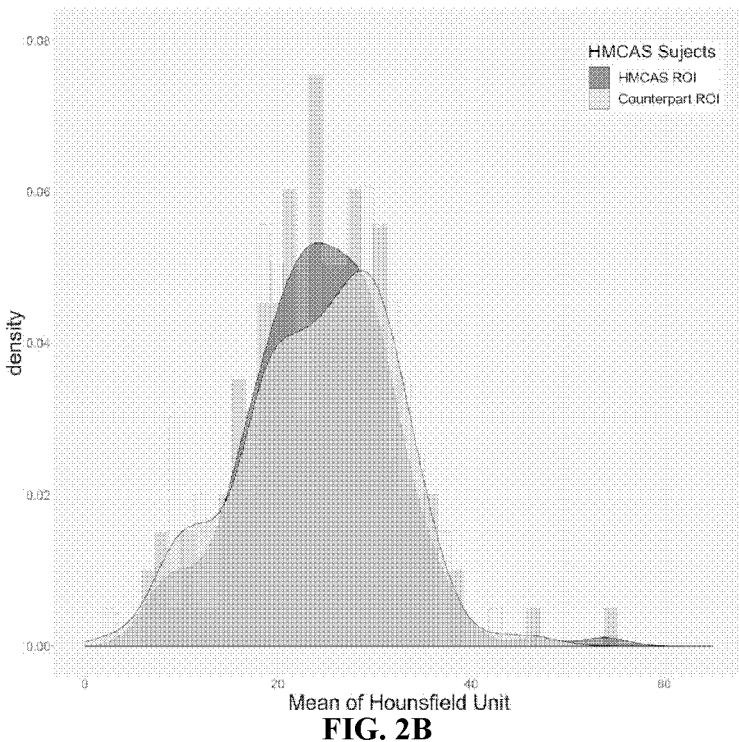

FIGS. 2A and 2B show two plots that aim to compare the histograms of mean HU values calculated from bilateral ROIs. FIG. 2A was drawn based on the NCCT from those 195 HMCAS subjects. For each NCCT volume, both the ROI of HMCAS and its mirrored counterpart within the contralateral hemisphere (HMCAS & Counterpart ROIs) were extracted. For each pair of ROIs, the mean HU values were calculated and plotted as two histograms with density curves. The histograms in FIG. 2B were generated for comparison purposes. An equal amount of subjects (195 cases) that had no HMCAS observed in their NCCT was randomly selected. Then those mirrored ROIs that were previously extracted from the HMCAS subjects were applied and covered onto the non-HMCAS. Calculations of mean HU values were repeated on newly extracted paired ROIs (Targeted & Counterpart ROIs) and histograms along with corresponding density curves were drawn. As shown in the figures, the mirrored regions demonstrate significant differences in HU values between subjects with and without HMCAS.

The following section shows the results of ablation studies to demonstrate the importance of various components of the proposed DSU-Net. In addition, results of choices of hyperparameters within the Tversky loss also indicate its effectiveness in dealing with the imbalance issue. Moreover, comparative studies with other state-of-the-art models revealed the superior performance of DSU-Net.

i. Effects of 3D Framework

To investigate the effectiveness of utilizing the contextual information along the slice dimension (depth) of a 3D CT image, experiments were conducted using 2D and 3D frameworks based on the baseline U-Net, SU-Net and DSU-Net. The segmentation results shown in Table I reveal that 3D architectures often performed better than their 2D counterparts based on all performance measures except MSD for the case of SU-Net. These indicated the superiority of the 3D frameworks, where the spatial contextual information would significantly improve models' performance.

TABLE I

| HMCAS segmentation results of ablation study of DSU-NET | | | | | |
|---|---|---|---|---|---|
| | DSC | Jaccard | Recall | Precision | ASSD | MSD |
| 2D U-Net | 0.638 ± 0.076 | 0.611 ± 0.084 | 0.806 ± 0.034 | 0.752 ± 0.092 | 10.931 ± 4.583 | 38.946 ± 14.596 |
| 3D U-Net | 0.714 ± 0.078 | 0.685 ± 0.086 | 0.810 ± 0.033 | 0.835 ± 0.078 | 9.396 ± 6.658 | 24.860 ± 8.773 |
| 2D SU-Net | 0.697 ± 0.043 | 0.670 ± 0.048 | 0.810 ± 0.034 | 0.822 ± 0.045 | 8.312 ± 5.210 | 20.855 ± 7.023 |
| 3D SU-Net | 0.746 ± 0.047 | 0.715 ± 0.052 | 0.822 ± 0.034 | 0.854 ± 0.049 | 5.101 ± 2.547 | 20.600 ± 8.893 |
| 2D DSU-Net | 0.727 ± 0.051 | 0.698 ± 0.059 | 0.818 ± 0.037 | 0.840 ± 0.046 | 6.942 ± 5.670 | 17.618 ± 6.391 |
| 3D DSU-Net | 0.784 ± 0.066 | 0.753 ± 0.067 | 0.841 ± 0.053 | 0.879 ± 0.044 | 4.627 ± 3.018 | 16.086 ± 8.166 |

SU-Net refers to Siamese-U-net and DSU-Net refers to Dissimilar-Siamese-U-Net ii. Effects of Siamese Module and Dissimilar Block To study the importance of the Siamese module in the proposed DSU-Net architecture, the SU-Nets, the U-Net models with the Siamese module were compared to their baseline U-Net models. As seen from Table I, both 2D and 3D SU-Nets performed better than their corresponding baseline U-Nets. The inclusion of Siamese module showed increments in DSC, Jaccard index, recall and precision, and reduction in ASSD and MSD. The shared-weights training scheme in both sub-networks allows the Siamese module to compare the features extracted from the left and right hemisphere ROIs.

Ablation studies on Dissimilar blocks were conducted by adding the proposed blocks on top of the SU-Nets. Like the previous study, the experiments were conducted under 2D and 3D frameworks as well. From Table I, all evaluation metrics obtained from the DSU-Nets surpassed their associated SU-Nets, indicating that the adoption of Dissimilar blocks improves the model performance.

Figure 3A:
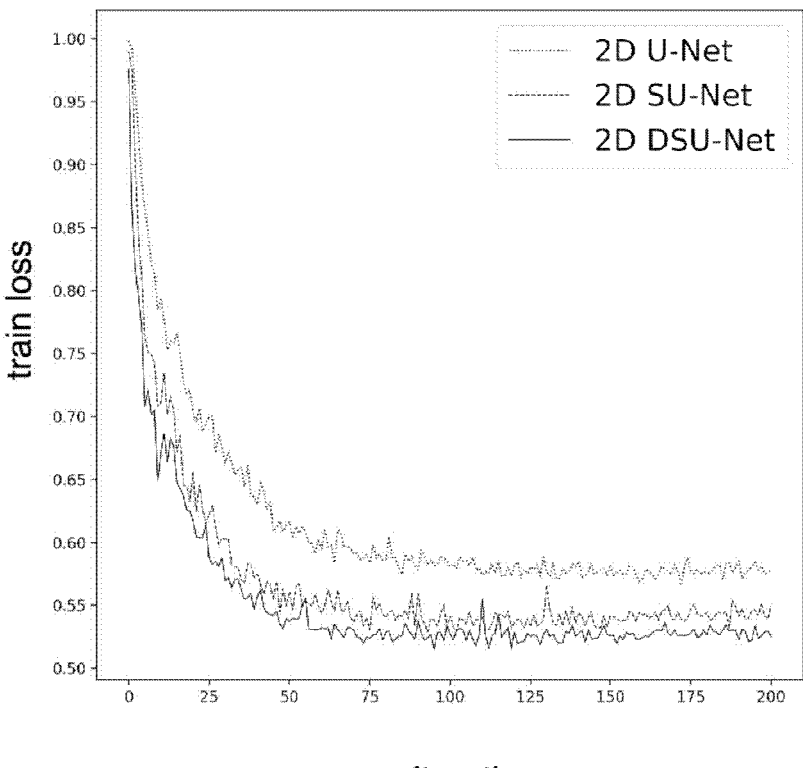
FIGS. 3A and 3B are line graphs showing validation losses of three U-nets with 2D-architectures (FIG. 3A) and 3D-architectures (FIG. 3B).
Figure 3B:
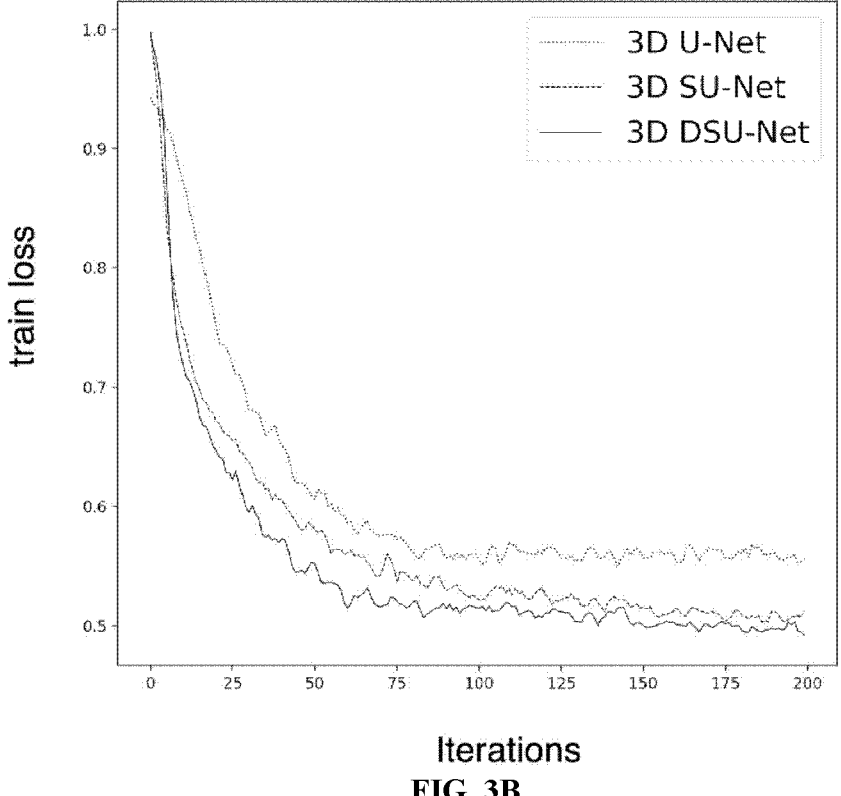

FIGS. 3A and 3B show the trace plots of the validation losses of three U-Net models with 2D (FIG. 3A) and 3D (FIG. 3B) architectures. The losses were obtained by averaging the validation losses of the described cross-validated experiments. Both trace plots demonstrate that the DSU-Nets converge faster than the SU-Nets and baseline U-Nets, and the baseline U-Nets performed the worst.

iii. Effects of Tversky Loss

Table II shows the performance of 3D DSU-Nets trained based on different choices of α and β in the Tversky loss function.

TABLE II

HMCAS segmentation results of different hyperparameters in Tversky loss

| | DSC | Jaccard | Recall | Precision | ASSD | MSD |
|---|---|---|---|---|---|---|
| α = 0.5, β = 0.5 | 0.754 ± 0.031 | 0.722 ± 0.035 | 0.816 ± 0.037 | 0.870 ± 0.031 | 4.600 ± 2.037 | 16.949 ± 6.093 |

TABLE II-continued

HMCAS segmentation results of different hyperparameters in Tversky loss

| | DSC | Jaccard | Recall | Precision | ASSD | MSD |
|---|---|---|---|---|---|---|
| α = 0.6, β = 0.4 | 0.764 ± 0.044 | 0.733 ± 0.050 | 0.824 ± 0.035 | 0.877 ± 0.046 | 4.069 ± 2.294 | 14.980 ± 6.316 |
| α = 0.7, β = 0.3 | 0.784 ± 0.066 | 0.753 ± 0.067 | 0.841 ± 0.053 | 0.879 ± 0.044 | 4.627 ± 3.018 | 16.086 ± 8.166 |
| α = 0.8, β = 0.2 | 0.749 ± 0.058 | 0.718 ± 0.064 | 0.826 ± 0.037 | 0.858 ± 0.062 | 4.378 ± 2.467 | 15.728 ± 7.458 |
| α = 0.9, β = 0.1 | 0.744 ± 0.045 | 0.712 ± 0.045 | 0.829 ± 0.039 | 0.849 ± 0.054 | 4.114 ± 1.984 | 14.400 ± 6.035 |

The results were obtained based on 3D DSU-Net. When α = 0.5, β = 0.5, Tversky loss is the same as the Dice loss.

The best performance was achieved when α=0.7 and β=0.3 where it gets the highest DSC and Jaccard index, recall and precision. Note that the commonly used Dice loss is a special case of Tversky where α=β=0.5. Models trained with the Tversky loss outperformed that trained with Dice loss. The adoption of such adjustable hyperparameters in the Tversky loss helps balance the emphasis on false positive and false negative predictions, thereby showing the advantage when dealing with an imbalanced dataset.

iv. Comparative Studies with State-of-the-Art Models

To demonstrate the superiority of proposed model, a comparative analysis was conducted with several state-of-the-art models. The HMCAS segmentation results shown in Table III demonstrate that 2D U-Net gives relatively comparable performance to the other four existing models and its performance is less superior compared to the 2D DSU-Net, indicating the inclusion of the proposed Siamese module and Dissimilar block does improve the performance in segmenting the HMCAS. Further, the proposed 3D DSU-Net outperformed 2D DSU-Net and the other state-of-the-art models, achieving the highest DSC, Jaccard index, recall and precision and the lowest ASSD and MSD.

TABLE III

Segmentation performance of comparative studies with several state-of-the-art methods[a]

| Models | DSC | Jaccard | Recall | Precision | ASSD | MSD |
|---|---|---|---|---|---|---|
| SegNet[b] | 0.649 ± 0.057 | 0.633 ± 0.057 | 0.770 ± 0.047 | 0.807 ± 0.047 | 13.115 ± 8.272 | 34.387 ± 17.217 |
| PSP Net[c] | 0.673 ± 0.055 | 0.658 ± 0.055 | 0.761 ± 0.050 | 0.841 ± 0.026 | 9.953 ± 3.487 | 30.529 ± 10.117 |
| DeepLabV3+[d] | 0.684 ± 0.047 | 0.658 ± 0.053 | 0.787 ± 0.038 | 0.812 ± 0.038 | 5.010 ± 1.959 | 18.833 ± 7.448 |
| Unet++[e] | 0.654 ± 0.058 | 0.627 ± 0.062 | 0.808 ± 0.042 | 0.769 ± 0.061 | 9.570 ± 4.513 | 34.376 ± 9.450 |
| 2D U-Net[f] | 0.638 ± 0.076 | 0.611 ± 0.084 | 0.806 ± 0.034 | 0.752 ± 0.092 | 10.931 ± 4.583 | 38.946 ± 14.596 |
| 2D DSU-Net | 0.727 ± 0.051 | 0.698 ± 0.059 | 0.818 ± 0.037 | 0.840 ± 0.046 | 6.942 ± 5.670 | 17.618 ± 6.391 |
| 3D DSU-Net | 0.784 ± 0.066 | 0.753 ± 0.067 | 0.841 ± 0.053 | 0.879 ± 0.044 | 4.627 ± 3.018 | 16.086 ± 8.166 |

[a]Only 3D DSU-NET adopted 3D framework while all other models utilized 2D frameworks.

[b]Tsang, et al., Int. J. of Stroke 2019, 15 (1), 69-74.

[c]You, et al., Frontiers in Neuroinformatics 2020, 14, 13.

[d]Dong, et al., Proc. IEEE Conf. Comput. Vis. Pattern Recognit. 2017, 1851-1860.

[e]Badrinarayanan, et al., IEEE trans. Pattern Anal. Mach. Intell. 2017, 39 (12), 2481-2495.

[f]Ronneberger, et al., Proc. Int. Conf. Med. Image Comput. Comput.-Assist. Intervent. 2015, 234-241.

The segmentation results for SegNet, PSP-Net, and 2D U-Net were poor with predicted segments distorted or missed. As for DeepLabV3+, its predictions suffered from the problem of dilation for small objects which is probably due to the use of atrous convolutions in DeepLabV3+. The proposed 2D/3D DSU-Nets gave satisfactory segmentation results and performed better than U-Net++.

Early recognition of HMCAS is helpful to facilitate in-patient triage and subsequent thrombolysis or thrombectomy treatment. Among all the medical imaging modalities, non-contrast head CT serves as the initial evaluation of patients with suspected acute ischemic stroke. Accurate segmentation of HMCAS on NCCT is challenging due to its low contrast of brain tissue on CT images and its proximity to bone structure or vascular calcifications in the brain. In such cases, even experienced neuroradiologists do not have sufficient high inter-rater reliability during the assessment stage. Existing deep learning models seldom evaluate the discrepancies between the left and right hemispheres, which is a key stroke-related feature identified by neuroradiologists. To address this limitation in the field, a deep Dissimilar-Siamese-U-Net has been developed, which incorporates the Siamese and U-Net architectures, and facilitates the input of data from bilateral hemispheres separately via two identical sub-networks with shared weights. Moreover, the newly introduced Dissimilar blocks fully leverage the feature representation of the dissimilarities between the left and right hemispheres, thereby enhancing the performance of the model. The current study was conducted using 624 annotated head NCCT volumes retrospectively collected from public hospitals in Hong Kong.

The HMCAS segmentation performances of various models were evaluated. The evaluation revealed that proposed 3D DSU-Net model outperformed current state-of-the-art models, including SegNet (Badrinarayanan, et al., *IEEE trans. Pattern Anal. Mach. Intell.* 2017, 39 (12), 2481-2495), PSP-Net (Zhao, et al., Proc. *IEEE Conf. Comput. Vis. Pattern Recognit.* 2017, 2881-2890), DeepLabV3 (Chen, et al., *Proc. Euro. Conf. Comput. Vis.* 2018, 801-818), and UNet++ (Zhou, et al., *Deep Learn. Med. Imag. Anal. Workshop* 2018, 3-11).

The HMCAS segmentation performances were evaluated on various current state-of-the-art models, including SegNet (Badrinarayanan, et al., *IEEE trans. Pattern Anal. Mach. Intell.* 2017, 39 (12), 2481-2495), PSP-Net (Zhao, et al., Proc. *IEEE Conf. Comput. Vis. Pattern Recognit.* 2017, 2881-2890), DeepLabV3 (Chen, et al., *Proc. Euro. Conf. Comput. Vis.* 2018, 801-818), and UNet++ (Zhou, et al., *Deep Learn. Med. Imag. Anal. Workshop* 2018, 3-11). Though several 3D models have been discussed in recent literatures, most of them are extensions of 2D frameworks and no one can be declared as the best choice. Thus, the performances of the models were compared based on 2D frameworks. The DSU-Net still outperformed all the state-of-the-art models.

The agreement on the annotations of HMCAS among experienced cerebrovascular specialists was assessed. A blinded cohort study of 324 patients collected in the second stage (discussed above) was conducted. Each NCCT volume was examined twice by non-overlapped cerebrovascular specialists, and both procedures were conducted independently and blindly (only NCCT was provided). Their agreements on segmentation annotation were measured by DSC, Jaccard index, ASSD and MSD which achieved 0.794, 0.760, 2.667 and 11.191, respectively. In addition, the detection of the presence of HMCAS (121 out of 324) by inter-rater reliability and Cohen's Kappa score was evaluated, which gave values of 0.867 and 0.680, respectively. The segmentation and the detection agreements were not sufficiently high, which are consistent with similar studies in the previous studies (Abul-Kasim, et al., *Neurology India* 2009, 57 (2), 143; Ernst, et al., *Neuroradiology* 2014, 56 (12), 1063-1068); thereby, indicating the challenge of our study. In order to explore the ability to detect the HMCAS, the segmentation predictions were converted to a binary indicator that can represent the presence of the HMCAS. A patient was predicted to have HMCAS present whenever there was an overlap between the predicted HMCAS region and the ground truth region. The detection accuracy, recall, specificity and precision were $0.867 \pm 0.029$, $0.732 \pm 0.152$, $0.923 \pm 0.049$ and $0.812 \pm 0.124$, respectively. The performance of the 3D DSU-Net in both segmentation and detection tasks was comparable to the human specialists.

The current studies also showed that the brain NCCT pre-processing step is heavily time-consuming. Depending on the number of scan slices (varies 30 to 400 slices per case), the process generally takes 3 to 7 minutes per case. This is largely due to the computational burden of matrix affine transformation procedure within the brain registration step. In this project, high quality of brain registration outcomes was chosen.

As discussed previously, the NCCT image data were collected in two stages (300 cases in the first stage and 324 cases in the second stage) and all the NCCT collected in the first stage were 5 mm-thick slices. In such cases subtle HMCAS might not be clearly observed or even be missed. Furthermore, training size can be expanded as less than one third of the patients have HMCAS (195 out of 624). It is believed that no public datasets are currently available for further method validation.

In spite of the superior performance demonstrated here, it is believed that performance could be further improved using larger training data and/or a more exhaustive selection of training hyper-parameters. Exploiting multiple NCCT templates with different slice thicknesses or in-plane resolutions could be a solution to speed up the pre-processing steps and improve the segmentation accuracy.

The proposed model design can be adapted to different imaging modalities, e.g. MR imaging, and solutions designed for similar tasks can be compared, thereby evaluating the extent to which the architecture should be modality specific. Moreover, aimed at exploring the feature representation of dissimilarities within bilateral hemispheres, the proposed method is also extendable to other studies that require bilateral comparisons, e.g. brain tumor detection, breast or prostate cancer detection, etc.

An end-to-end automated approach capable of a fast and reliable segmentation of the hyperdense middle cerebral artery sign on non-contrast enhanced CT is described. Preferably, the proposed method utilizes twin sub-networks with shared weights for bilateral hemispheres. The newly designed Dissimilar block module effectively explores the discrepancies between the left and right hemispheres, which is not implemented by most deep learning segmentation approaches. The automated algorithm outperformed several state-of-the-art methods, demonstrating its feasibility and potential for application in deep learning for segmenting and diagnosing HMCAS on NCCT in stroke patients. The NCCT data involved in this study were acquired through a variety of CT scanners from multiple clinical institutions, demonstrating that the proposed system is robust and consistent with variations of image characters, thereby further demonstrating its broad applicability in image processing settings, including clinical settings. These findings are important and support the clinical application of the system as a diagnostic adjunct in the detection of acute stroke, especially in resource-limited settings when immediate expert neuroradiological interpretation is not readily available.

The current study has the following non-limiting benefits:

(1) The Siamese module with shared weights facilitates the incorporation of features from both left and right brain images, thereby enhancing the capability of abnormality detection of ischemia stroke and increasing computational efficiency;

(2) The proposed Dissimilar block effectively probes feature representation of the dissimilarity between the bilateral hemispheres. The extracted features significantly improve the model performance on EIMCAS segmentation;

(3) The fully automated image pre-processing procedure allows geometrical alignment of all brain images to a predefined template, thereby assuring the symmetricity of brain CT images and further development of the model to focus on specific candidate regions of interest; and (4) The study subjects involved in this research were chosen based on a territory-wide sampling of stroke patients from multiple hospitals within the public health system of Hong Kong. The NCCT scans were obtained from different CT scanners with different settings. This demonstrates that the proposed system can be applied to images with various characters, demonstrating broad applicability in clinical settings.

Those skilled in the art will recognize, or be able to ascertain using no more than routine experimentation, many equivalents to the specific embodiments of the invention described herein. Such equivalents are intended to be encompassed by the following claims.

We claim:

1. A computer-implemented system (CIS) comprising:

(i) two segmentation architectures independently comprising neural networks, and (ii) a Dissimilar block operably linked to the two segmentation architectures, wherein the Dissimilar block comprises a tool that compares features in data from corresponding blocks in the two segmentation architectures, wherein the Dissimilar block is operably linked to (a) at least two encoding blocks, one in each of the two segmentation architectures and (b) at least one decoding block in the two segmentation architectures, and wherein the Dissimilar block is capable of transmitting encoding features received from the at least two encoding blocks to the at least one decoding block.

2. The CIS of claim 1, wherein the neural networks have shared weights.

3. The CIS of claim 1, wherein the neural networks independently comprise image segmentation architectures.

4. The CIS of claim 1, wherein the neural networks independently comprise an encoding path, a decoding path, or both.

5. The CIS of claim 4, wherein the encoding path and the decoding path are connected via the Dissimilar block through one or more skip connections.

6. The CIS of claim 4, wherein:

(i) the encoding path comprises a series of encoding blocks, wherein the encoding blocks independently comprise one or more convolution layers, activation function layers, max pooling layers, or a combination thereof, or (ii) the decoding path comprises a series of decoding blocks, wherein the decoding blocks independently comprise one or more up-sampling layers, concatenation layers, convolutional layers, activation function layers, or a combination thereof.

7. The CIS of claim 6, wherein at least one of the one or more activation function layers comprises a non-linear function.

8. The CIS of claim 6, wherein one of the one or more activation function layers are a parametric rectified linear unit activation function (PReLu) layer, a rectified linear unit activation function (ReLu) layer, or a sigmoid activation function layer.

9. The CIS of claim 6, wherein the Dissimilar block connects corresponding encoding blocks within the encoding paths of the two or more segmentation architectures.

10. The CIS of claim 1, wherein the neural networks are independently U-net neural networks, optionally 3D-Unet neural networks.

11. The CIS of claim 1, having the two segmentation architectures on a Siamese framework.

12. The CIS of claim 11, comprising neural networks that comprise 3D-Unet neural networks, wherein the 3D-Unet neural networks independently comprise:

(i) a series of encoding blocks, wherein the encoding blocks comprise two or more consecutive convolution layers, wherein the last convolution layers in a down-sampling arm of at least one of the 3D-Unet neural networks connect with one or more sigmoid activation function layers, (ii) a series of decoding blocks comprising one or more up-sampling layers that utilize bilinear interpolation with a stride size of two, or (iii) both (i) and (ii).

13. The CIS of claim 12, wherein the decoding blocks comprise a concatenation layer connected to the one or more up-sampling layers and the Dissimilar block via a skip connection.

14. The CIS of claim 12, wherein the other consecutive convolution layers connect with one or more PRELU activation function layers.

15. A computer-implemented method (CIM) for analyzing data, the CIM comprising:

(a) visualizing on a graphical user interface, output from the CIS of claim 1, optionally wherein the data are images of one or more biological samples.

16. The CIM of claim 15, wherein visualizing the output on the graphical user interface, provides a diagnosis, prognosis, or both, of a disease or disorder in a subject.

17. The CIM of claim 16, wherein:

(i) the disease or disorder is acute ischemic stroke or thromboembolus, or (ii) the output comprises an image containing a middle cerebral artery.

18. The CIM of claim 15, wherein the CIM comprises providing to the CIS, prior to step (a), images from two biological organs that occur in pairs in a mammal, or from separate segments of a biological organ that has bilateral symmetry.

19. The CIM of claim 18, further comprising repositioning the images into a reference coordinate system, optionally wherein the reference coordinate system is a stereotaxic coordinate system.

20. The CIM of claim 15, wherein the data are selected from the group consisting of computed tomography (CT) scans, X-ray images, magnetic resonance images, ultrasound images, positron emission tomography images, magnetic resonance angiograms, and combinations thereof.

* * * * *